United States Patent [19]

Gruber et al.

[11] 3,953,462

[45] Apr. 27, 1976

[54] IMAGING PROCESS

[75] Inventors: Robert J. Gruber, Pittsford; Nicholas J. Germano, Fairport, both of N.Y.

[73] Assignee: Xerox Corporation, Stamford, Conn.

[22] Filed: Oct. 29, 1973

[21] Appl. No.: 411,596

[52] U.S. Cl. ................................ 260/295 A; 96/1.3

[51] Int. Cl.[2] ........................................ C07D 405/04

[58] Field of Search .............................. 260/295 A

[56] References Cited

UNITED STATES PATENTS

| | | | |
|---|---|---|---|
| 3,447,922 | 6/1969 | Weinberger | 204/181 |
| 3,658,985 | 4/1972 | Olson et al. | 8/10.1 |
| 3,666,812 | 5/1972 | Kalopissis | 8/10.1 |

OTHER PUBLICATIONS

Chemical Abstracts 68:3914r (1968).
Chemical Abstracts 71:92756t (1969).
Chemical Abstracts 72:3301w (1970).
Chemical Abstracts 74:65602v (1971).

*Primary Examiner*—Norman A. Drezin
*Attorney, Agent, or Firm*—James J. Ralabate; David C. Petre; Richard A. Tomlin

[57] ABSTRACT

3-Bromo-N-2″-pyridyl-8,13-dioxodinaphtho-(2,1-b;3′,3′-d)-furan-6-carboxamide is described as a new composition of matter along with its use in electrophotographic and photoelectrophoretic imaging processes.

1 Claim, 1 Drawing Figure

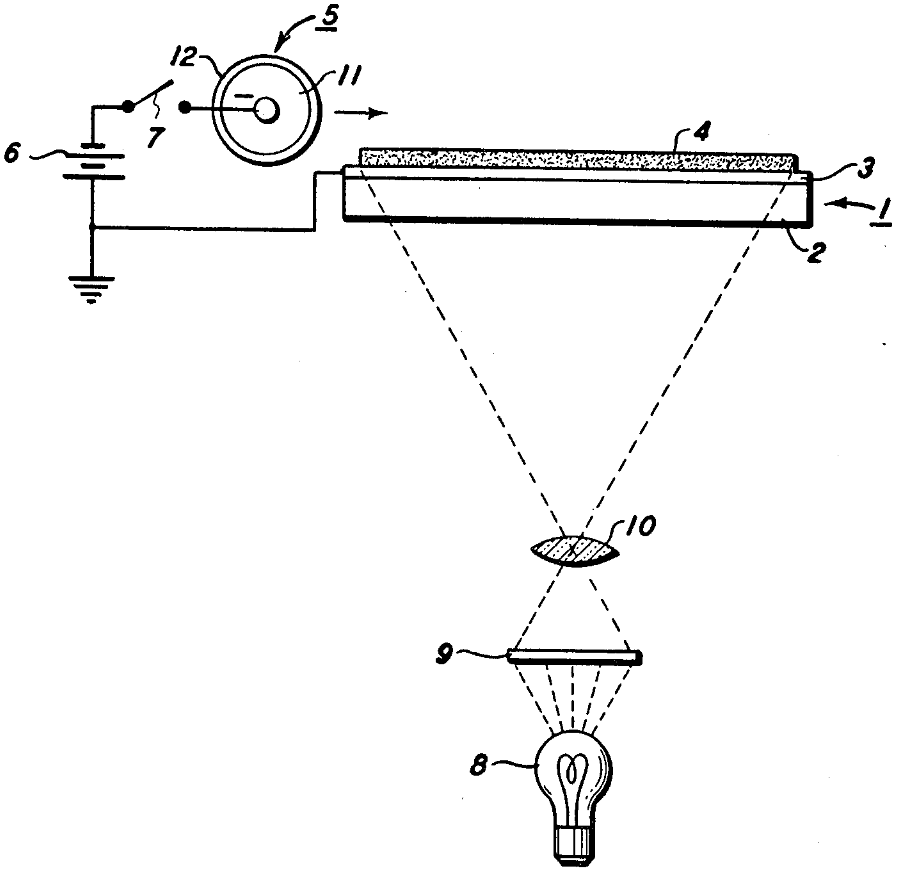
5
12
11
7
6
4
3
1
2
10
9
8

IMAGING PROCESS

BACKGROUND OF THE INVENTION

The invention relates in general to electrophotographic and photoelectrophoretic imaging systems. More specifically, the invention concerns 3-bromo-N-2''-pyridyl-8,13-dioxodinaphtho-(2,1-b; 2',3'-d)-furan-6-carboxamide as a new composition of matter and its use in photoelectrophoretic imaging.

In general the phrase photoelectrophoretic imaging, as used herein, refers to those systems wherein electrically photosensitive particles dispersed in an insulating carrier liquid are exposed to imagewise light and an electrical field resulting in particle migration in image configuration. One such process which is capable of producing one color image, or images, in more than one color including full natural color in one step is described in detail and claimed in U.S. Pat. Nos. 3,383,993 to Yeh; 3,384,488 and 3,384,565 to Tulagin and Carreira and 3,384,566 to Clark, all issued May 21, 1968, the entire disclosures of which are incorporated herein by reference. In such an imaging system, electrically photosensitive particles are dispersed in a relatively non-conductive liquid carrier. The suspension is placed between electrodes, subjected to a potential difference and exposed to an image. As these steps are completed, selective particle migration takes place in image configuration. Where the electrical field is applied between electrodes which are in contact with the imaging suspension, normally images made up of particles are formed on one or both electrodes. In a monochromatic system, particles of only one color need be used, but particles of additional colors may be used if desired to provide a range of monochrome colors which may be reproduced. In a polychromatic system, images of more than one color may be formed by utilizing particles of more than one color which have spectral response curves which do not have substantial overlap thereby providing for color separation. In a preferred embodiment for subtractive full color imaging, yellow particles responsive to blue light, cyan particles responsive to red light and magenta particles responsive to green light are used in the suspension. Thus, when the suspension is exposed to red light, for example, the red light causes the cyan particle to move away from the surface on which the image is formed leaving behind the yellow and magenta particles which combined appear red. Further, where white light impinges the suspension, all particles migrate leaving a clear area which when the image is transferred to white paper appears white. Also, where no light impinges the suspension, all particles remain which form a dark brown or black area.

The critical component of such an imaging system is the electrically photosensitive particles. The particles must have intense and pure colors to form highly saturated images. For monochrome imaging, it is desirable that the particles be highly photosensitive so that light and power requirements are small. The requirements for polychromatic imaging are, however, much more severe in that the particles of each color cyan, yellow and magenta, for example, must have intense and pure colors and must have spectral response curves which are well-defined and do not overlap the spectral response curves for particles of other colors. Further, the photoresponse of a given particle must be to approximately the same intensity of exposure as the other particles to provide color balanced images. For example, in a subtractive system, if a particle is too photoresponsive or has too broad a spectral response, the final image will be deficient in that color. Conversely, where the particle is too "slow", the image will have a high background of that color and will have poor color balance. For additive systems, the results would be reversed.

SUMMARY OF THE INVENTION

It is, therefore, an object of this invention to provide a new pigment composition.

It is another object of this invention to provide photoelectrophoretic imaging systems which have improved photoelectrophoretic imaging characteristics.

It is another object of this invention to provide a new electrically photosensitive particle for photoelectrophoretic imaging.

The foregoing objects and others are accomplished in accordance with this invention by providing photoelectrophoretic imaging processes in which 3-bromo-N-2''-pyridyl-8,13-dioxodinaphtho-(2,1-b;2',3'-d)-furan-6-carboxamide is used as a yellow pigment. The compound has the following formula:

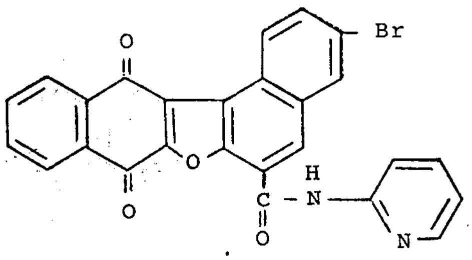

This compound may also be referred to as 3-bromo-8,13-dihydro-8,13-dioxo-N-2-pyridyl-dinaphtho[2,1-b;2',3'-d]furan-6-carboxamide.

The above compound has an intense and pure yellow color and an unusually high photosensitive response.

In a preferred photoelectrophoretic imaging process, finely divided particles of electrically photosensitive materials are dispersed in an insulating carrier liquid and coated onto a transparent conductive electrode called the "injecting" electrode. A second electrode having an insulating outer surface and called a "blocking" electrode is caused to contact the free surface of the suspension. An electrical field of relatively high potential is applied across the suspension between the electrodes while the suspension is exposed through the injecting electrode to a pattern of electromagnetic radiation of wavelengths to which at least some of the particles are responsive. On completion of these steps, normally a positive image is found adhering to the injecting electrode and a negative image is formed on the blocking electrode. Apparently, the particles which are within interaction range of the conductive electrode when struck by light to which they are sensitive exchange charge with the injecting electrode, are repelled by it and adhere to the blocking electrode insulating surface leaving behind a positive image. The particles on the surface of the blocking electrode are less able to exchange charge with the insulating surface and remain thereon forming a negative image.

The process of photoelectrophoretic imaging and the materials used are set out in detail in the above mentioned U.S. Pat. Nos. 3,383,993, 3,384,488, 3,384,565 and 3,384,566.

The compound of the present invention is useful as a pigment wherever there is a need for an intense yellow coloration. Additionally, the compound is highly photosensitive and suitable for use in a wide variety of imaging systems.

Typical of the imaging systems which can utilize the present compound are those in which images are formed using light and electrical field. For example, the compound may be used in xerographic processes as originally described in U.S. Pat. No. 2,297,691 to C. F. Carlson. The electrically photosensitive compound of this invention may be used as a photoconductor either alone or dispersed in a binder. The electrically photosensitive material of the present invention may be used in deformation imaging. Deformation imaging is inclusive of frost and relief imaging systems. Frost imaging is described in detail in a publication entitled, "A Cyclic Xerographic Method Based on Frost Deformation", by R. W. Gundlach and C. J. Claus, *Journal of Photographic Science and Engineering*, January-February, 1963. Relief imaging is described in detail in U.S. Pat. Nos. 3,055,006, 3,163,872 and 3,113,179.

Other imaging systems which can utilize the present crons in average cross section are preferred although particles up to 5 or 10 microns may be used. Larger particles may be used for special purposes where high resolution is not required.

The concentration of particles dispersed in the liquid depends on a number of variables including operating conditions, the density of the final image desired, the use to which the image is to put, the solubility of added dispersants and other factors generally known to those skilled in the art of ink or plastic coating formulation.

The transparent conductive substrate may comprise any suitable material. Typical transparent, conductive materials include conductively coated glass, such as aluminum or tin oxide coated glass or transparent plastic materials such as polyester films overcoated with conductive materials and cellophane.

The insulating surface for the blocking electrode may be paper, cloth, rubber, plastics, both thermoplastic or thermosetting or other insulating materials.

The compound of the present invention may be made by any conventional method. The preferred method is to react 2,3-dichloro1,4-naphthoquinone with 6-bromo-2-hydroxy-3(2′-pyridyl)naphthamide as follows:

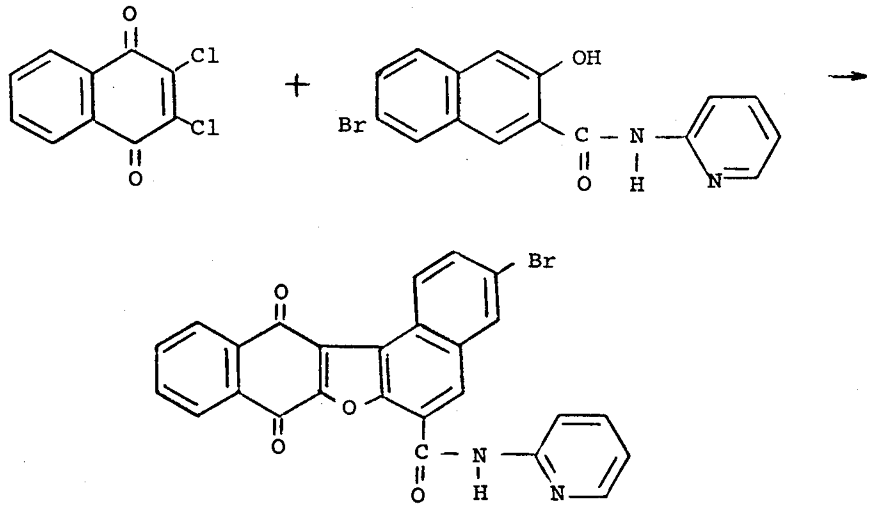

compound are migration imaging as described, for example, in U.S. Pat. No. 3,520,681 and manifold imaging as described in U.S. Pat. No. 3,707,368.

The pigment of the present invention, however, is most useful for polychromatic photoelectrophoretic imaging as described above.

The carrier liquid for the imaging of this invention may comprise any suitable material. Typical insulating materials include liquids, or solids which may be converted to a liquid at the time of imaging. Typical materials include: decane, dodecane, tetradecane, kerosene, molten paraffin, molten beeswax or other molten thermoplastic material, mineral oil, silicone oils such as dimethyl polysiloxane, fluorinated hydrocarbons and mixtures thereof. Mineral oil and kerosene are preferred because of their excellent insulating qualities.

It is desirable to use particles which are relatively small in size because small particles provide more covering power and a more stable suspension and provide images of higher resolution than would be possible with larger particles. Particles of less than one or two mi-

EXAMPLE I

The above reaction is carried out as follows:

In a 5-liter, three-necked round bottom flask fitted with a heating mantle, thermometer, water condenser and mechanical stirrer is placed about 70 grams of 6-bromo-2-hydroxy-3(2′-pyridyl)naphthamide, about 47.6 grams of 2,3-dichloro-1,4-naphthoquinone dissolved in about 460 ml of dimethylacetamide, about 77.6 grams of anhydrous powdered sodium carbonate and about 460 ml of isopropropanol under a nitrogen blanket. The mixture is slowly heated to reflex and held at reflex for about 2½ hours. The reaction mixture is filtered hot providing a yellow cake. The resulting filter cake is washed with acetone until the filtrate is pale yellow. The cake is then washed with about 1500 ml of deionized water. The water washing is continued by 3 times forming a slurry with 2100 ml of deionized water at a temperature between 80° and 90°C for 1 hour and then filtered hot. Further washing with 500 ml of acetone is used to aid drying. Final dry weight is about 62 grams. The dried pigment is subsequently purified by crystallizing from quinoline or pyridine.

BRIEF DESCRIPTION OF THE DRAWING

The advantages obtained from the use of the instant compound in a photoelectrophoretic imaging system will become apparent upon consideration of the detailed disclosure of this invention, particularly when considered in conjunction with the accompanying FIGURE which is a side sectional view of a simple exemplary photoelectrophoretic imaging system.

The sizes and shapes in the drawing should not be considered as actual sizes or even proportional to actual sizes because many of the elements have been purposely distorted in size to more fully and clearly describe the invention.

Referring now to the Figure, there is seen a transparent electrode generally designated 1, which in this exemplary instance, is made up of a layer of optically transparent glass 2 overcoated with a thin optically transparent layer 3 of tin oxide, commercially available under the name NESA glass. This electrode will be referred to as the injecting electrode. Coated on the surface of injecting electrode 1 is a thin layer 4 of finely divided photosensitive particles dispersed in an insulating liquid carrier. The term "electrically photosensitive", for the purposes of this application, refers to the properties of a particle which, when brought into interaction range of the injecting electrode, will migrate away from it under the influence of an applied electric field when it is exposed to radiation to which it is responsive. Liquid suspension 4 may also contain a sensitizer and/or a binder for the particles which is at least partially soluble in the suspending or carrier liquid. Adjacent to the liquid suspension 4 is a second electrode 5, "blocking electrode" which is connected to one side of potential source 6 through switch 7. The opposite terminal of potential source 6 is connected to the injecting electrode and ground so that when switch 7 is closed, an electrical field is applied across the liquid suspension 4 between electrodes 1 and 5. An image projector made up of light source 8, a transparency 9 and a lens 10 is provided to expose the suspension 4 to a light image of the original transparency 9 to be reproduced. Alternatively, the image may be light reflected off of an opaque picture or document. Electrode 5 is in the form of a roller having a conductive central core 11 connected to potential source 6. The core is covered with a layer of an insulating material 12. The suspension is exposed to the image to be reproduced while a potential is applied across the blocking and injecting electrodes by closing switch 7 and causing roller 5 to roll across the free surface of suspension 4 during imagewise exposure. On completion of roller traverse, a positive image is found on electrode 1 and a negative image is found on surface 5.

During roller transverse, the roller is pressed into virtual contact with the injecting electrode surfaces. Gaps of up to about one mil are used. Voltages of from about 300 to 5,000 volts are used in the apparatus as shown in the Figure.

DESCRIPTION OF THE PREFERRED EMBODIMENTS

The following Examples further specifically illustrate the improved photoelectrophoretic imaging system using the compositions of this invention. Parts and percentages are by weight unless otherwise indicated. Examples II through IV are carried out in an apparatus of the general type illustrated in the figure with the imaging suspension coated on the conductive surface of a NESA glass plate through which exposure is made. The NESA glass surface is connected to a source of high d.c. potential and ground. The other terminal of the source of high potential is connected to a steel roller about one inch in diameter having a ¾ inch layer of polyurethane having a resistivity of about 5 $\times 10^8$ ohm-cm forming a 2½ inch roller. A paper sheet is placed over the plastic to receive migrating particles. The particles are dispersed in the liquid carrier and ball milled until the average particle size is less than about one micron and a stable suspension is formed. The roller is moved across the plate surface at a rate of about 3 inches/second and the image is projected using a conventional tungsten lamp. The transparency may be black and white or color as indicated.

EXAMPLE II

Approximately 5 parts by weight of the compound of this invention is added to about 3 parts by weight Bonadur Red B, an insolubilized azo dye C.I. 15865 with calcium substituted in place of the sodium to insolubilize it as the magenta pigment and about 1 part of vanadyl phthalocyanine as the cyan pigment in about 100 parts of mineral oil. The suspension is exposed using a "Kodachrome" color transparency as the image input. The mixture is coated onto the NESA glass plate to a thicknes of about 2 mils. Roller potential is about 2,500 volts, the roller being biased negative with respect to the NESA glass plate. On completion of roller traverse, a high quality full color image is found on the surface of the NESA glass plate.

EXAMPLE III — PRIOR ART

The above experiment is repeated except that the yellow pigment is N-2″-pyridyl-8,13-dioxodinaphtho-(2,1-b;2′,3′-d)-furan6-carboxamide as shown in U.S. Pat. No. 3,447,922. A comparison of the results obtained using the prior art yellow compound which is the best known to Applicants and the yellow compound of this invention show an improvement in optical compatability with the cyan and magenta pigments. Images prepared using the yellow pigment of this invention show an improved range and accuracy of green reproduction. These characteristics are extremely important for a full color subtractive imaging process where accurate color separation and reproduction are required. The spectral imaging response edge for the compound of the present invention has been found to be moved toward the blue region approximately 20–25 nanometers relative to that of the prior art pigment.

EXAMPLE IV

The experiment of Example II is repeated with the exception that only particles of the yellow compound of this invention are suspended in the mineral oil and using a black and white transparency as image input, i.e., the suspension is exposed to light projected through the black and white transparency and the NESA glass plate. On completion of roller traverse, a positive yellow image is found on the NESA glass and a negative image is formed on the blocking roller electrode surface.

Although specific components and proportions have been described in the above Examples, other suitable materials, as listed above, may be used with similar results. In addition, other materials may be added to the pigment compositions to synergize, enhance or otherwise modify their properties. The pigment compositions where desired, for example, may be coated with a plastic.

Other modifications and ramifications of the present invention will occur to those skilled in the art upon a reading of the present disclosure. These are intended to be included within the scope of this invention.

What is claimed is:

1. 3-bromo-N-2''-pyridyl-8,13-dioxodinaphtho-(2,1-b; 2',3'-d)-furan-6-carboxamide which is represented by the formula

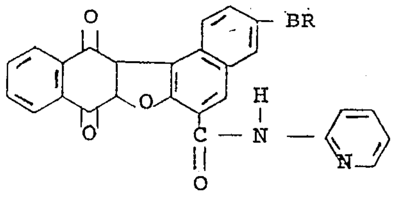

* * * * *